United States Patent [19]

Yokoshima et al.

[11] Patent Number: 4,783,544

[45] Date of Patent: Nov. 8, 1988

[54] DI-(METH)ACRYLIC ACID ESTER, RESIN COMPOSITION COMPRISING THE SAME AND COATING AGENT COMPRISING THE SAME

[75] Inventors: Minoru Yokoshima, Asa; Tetsuo Ohkubo, Ube; Masayuki Kiyomoto, Asa, all of Japan

[73] Assignee: Nippon Kayaku Kabushiki Kaisha, Tokyo, Japan

[21] Appl. No.: 875,064

[22] Filed: Jun. 17, 1986

[30] Foreign Application Priority Data

Jun. 19, 1985 [JP] Japan .................. 60-131631
Jun. 19, 1985 [JP] Japan .................. 60-131632
Sep. 6, 1985 [JP] Japan .................. 60-195725

[51] Int. Cl.$^4$ .................. C08F 2/50; C08F 218/00
[52] U.S. Cl. .................. 558/267; 350/96.29; 522/96; 522/183; 526/314; 558/276
[58] Field of Search ............... 522/183; 558/267, 276; 526/314

[56] References Cited

U.S. PATENT DOCUMENTS

| | | | |
|---|---|---|---|
| 3,716,571 | 2/1973 | Berlin .................. | 526/313 |
| 3,785,850 | 1/1974 | Parker .................. | 558/267 |
| 4,076,742 | 2/1978 | Berlin .................. | 558/267 |
| 4,107,386 | 8/1978 | Gruber .................. | 526/314 |
| 4,126,737 | 11/1978 | Gruber .................. | 526/313 |
| 4,144,262 | 3/1979 | Stevens .................. | 558/267 |
| 4,217,297 | 8/1980 | Lindner .................. | 558/267 |
| 4,246,336 | 1/1981 | Berlin .................. | 522/183 |
| 4,264,752 | 4/1981 | Watson .................. | 522/90 |
| 4,629,287 | 12/1986 | Bishop .................. | 522/96 |

FOREIGN PATENT DOCUMENTS

83185 6/1983 European Pat. Off. .
0141330 10/1983 European Pat. Off. .
0111280 12/1983 European Pat. Off. .
2375271 12/1976 France .

*Primary Examiner*—John C. Bleutge
*Assistant Examiner*—Arthur H. Koeckert
*Attorney, Agent, or Firm*—Birch, Stewart, Kolasch & Birch

[57] ABSTRACT

Disclosed herein are (i) a resin composition comprising (A) a di-(meth)acrylic acid ester of a carbonate diol having an average molecular weight of 500 to 3000 or of an addition compound of the carbonate diol with an ε-caprolactone, (B) a monoethylenically unsaturated monomer and optionally, (C) an initiator of photopolymerization, (ii) a di-(meth)acrylic acid ester of an addition compound of a carbonate diol having an average molecular weight of 500 to 3000 with an ε-caprolactone and (iii) a di-(meth)acrylic acid ester represented by the formula:

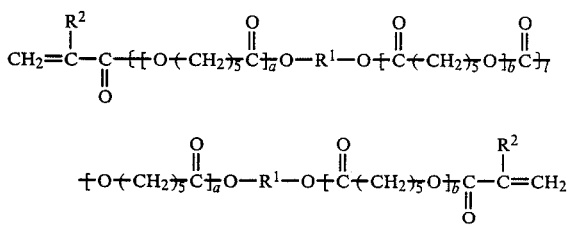

wherein $R^1$ represents an alkylene group having 4 to 10 carbon atoms, $R^2$ represents a hydrogen atom or a methyl group, the mean values of a and b are 0 to 5, respectively, the mean sum of a plus b is 0.5 to 5 and the mean value of l is 1 to 10.

3 Claims, No Drawings

DI-(METH)ACRYLIC ACID ESTER, RESIN COMPOSITION COMPRISING THE SAME AND COATING AGENT COMPRISING THE SAME

BACKGROUND OF THE INVENTION

The present invention relates to a novel di-(meth)acrylic acid ester, a resin composition comprising the same and a coating agent for optical glass fiber for use in transmitting light.

Since the optical fibers have a large capacity of transmitting informations and do not relatively receive interferences from outside, the use thereof has been remarkably increased, particularly in the field of communication in the recent years. The optical fibers are generally made of glass, because they are used in the field of communication. However, since the glass fibers are frangible and chemically damaged by water vapour, they are easily broken and their handling is difficult. Accordingly, the optical glass fibers have hitherto been coated with a resinous material. As such a resinous coating material, epoxy resin, urethane resin or the like has hitherto been used, however, much time is needed to cure such a resin and therefore, the producibility of coated glass fibers is poor. Further, since cured resin lacks pliability, the coated glass fibers have the disadvantage of losing the transmitting property due to side pressure.

In recent years, in order to remove the abovementioned disadvantage, a composition curable by ultraviolet rays containing urethane acrylate has been studied and examined, and a composition curable by ultraviolet rays for coating the optical glass fibers and a method for forming a coating film therefrom have been proposed, for instance, in Japanese Patent Application Laying-Open (KOKAI) No. 58-223638 (1983) and Canadian Patent No. 1198083.

Although the composition curable by ultraviolet rays, which has been used at present has the advantage of a high curing rate and also has the advantage that some desired properties can be reproduced easily and accurately, because of the large hygroscopic property this composition, a glass fiber coated with such a composition is apt to be spoiled by water and the coated glass fiber has the disadvantage that its physical properties change very much in the case where the temperature changes from $-60°$ to $80°$ C. thereby causing an increase in transmission loss.

As a result of the present inventors' studies for solving the above-mentioned problems, the present inventors have found that a novel resin composition comprising a novel di-(meth)acrylic acid ester has a high curing speed, provides a soft resin film of low hygroscopicity which has stable physical properties, which does not change between low and high temperature, and which has low glass-transition temperature and, this novel resin composition is suitable for coating an optical glass fiber for transmitting light based on the present invention is these findings.

DETAILED DESCRIPTION OF THE INVENTION

The present invention relates to (i) a resin composition comprising (A) a di-(meth)acrylic acid ester of a carbonate diol having an average molecular weight of 500 to 3000 or of an addition compound of the carbonate diol with ε-caprolactone, (B) a monoethylenically unsaturated monomer and as an optional component, (C) an initiator of photopolymerization, (ii) a coating agent for optical glass fiber comprising (A) a di-(meth)acrylic acid ester of a carbonate diol having the average molecular weight of 500 to 3000 or of an addition compound of the carbonate diol with ε-caprolactone, (B) a monoethylenically unsaturated monomer and (C) an initiator of photopolymerization, (iii) a di-(meth)acrylic acid ester of an addition compound of a carbonate diol having an average molecular weight of 500 to 3000 with ε-caprolactone and (iv) a di-(meth)acrylic acid ester represented by the formula (I):

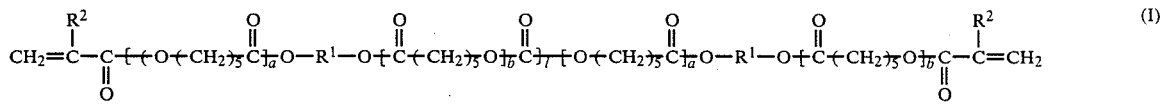

wherein $R^1$ represents an alkylene group having 4 to 10 carbon atoms, preferably 5 to 8 carbon atoms, $R^2$ represents a hydrogen atom or a methyl group, each mean value of a and b are 0 to 5, preferably 0 to 2, the mean sum of a plus b is 0.5 to 5, preferably 0.5 to 3 and the mean value of l is 1 to 10, preferably 3 to 8.

In the resin composition or a coating agent for optical glass fiber according to the present invention, it is preferable to use the di-(meth)acrylic acid ester (A) in a range of 5 to 80% by weight, particularly 10 to 70% by weight, and to use the monoethylenically unsaturated monomer (B) in a range of 20 to 80% by weight, particularly 30 to 60% by weight.

In addition, it is preferable to use the initiator of photopolymerization in a range of 0 to 10% by weight in the resin composition ordinarily, and in the coating agent, it is preferable to use the initiator of photopolymerization in a range of 0.1 to 10% by weight, particularly 1 to 5% by weight.

The following resin composition and the coating agent according to the present invention are exemplified.

(1a) A resin composition comprising (A) a di-(meth)acrylic acid ester of an addition compound of a carbonate diol having an average molecular weight of 500 to 3000 with ε-caprolactone, (B) a monoethylenically unsaturated monomer and, as an optional component, (C) an initiator of photopolymerization, (2a) A coating agent for optical glass fiber, comprising (A) a di-(meth)acrylic acid ester of an addition compound of a carbonate diol having an average molecular weight of 500 to 3000 with ε-caprolactone, (B) a monoethylenically unsaturated monomer and (C) an initiator of photopolymerization.

(1b) A resin composition comprising (A) a di-(meth)acrylic acid ester of a carbonate diol having an average molecular weight of from 500 to 3000, (D) polyurethane (meth)acrylate, (B) a monoethylenically unsaturated monomer and, as an optional component, (C) an initiator of photopolymerization, (2b) A coating agent for optical glass fiber comprising (A) a di-(meth)acrylic acid ester of a carbonate diol having an average molecular weight of 500 to 3000, (D) polyurethane (meth)acrylate, (B) a monoethylenically unsaturated monomer and (C) an initiator of photopolymerization.

Di-(meth)acrylic acid ester of the addition compound of a carbonate diol having an average molecular weight of 500 to 3000 with ε-caprolactone according to the present invention is produced, for instance, by reacting an addition compound (a), which is obtained by reacting a carbonate diol having an average molecular weight of 500 to 3000 with ε-caprolactone, with (meth)acrylic acid (b). A concrete example of the process for producing the above-mentioned di-(meth)acrylic acid ester is shown as follows.

To 0.5 mol of the addition compound obtained by reacting the carbonate diol with ε-caprolactone, preferably 1.0 to 2.0 mol, more preferably 1.0 to 1.5 mol of (meth)acrylic acid, preferably 0.01 to 5% by weight of a catalyst of esterification, for instance, p-toluenesulfonic acid, sulfuric acid or methanesulfonic acid, and a polymerization prohibitor, for instance, methoquinone, hydroquinone, phenothiazine or the like are added, the thus prepared mixture is heated preferably to a temperature of 70° to 130° C., and after dehydrating the mixture, the thus dehydrated mixture is washed with an alkali and water, and the low-boiling matters are removed by distillation from the thus washed mixture to produce the di-(meth)acrylic acid ester.

The carbonate diol which is the starting material in the case of producing the addition compound (a) may be produced, for instance, as follows.

Namely, the carbonate diol is obtained by an ester exchange reaction of a diaryl carbonate such as diphenyl carbonate; bischlorophenyl carbonate; dinaphthyl carbonate; phenyl tolyl carbonate; phenyl chlorophenyl carbonate and 2,4-ditolyl carbonate or a dialkyl carbonate such as diethyl carbonate and dimethyl carbonate with a diol, for instance, 1,6-hexanediol; neopentyl glycol; 1,4-butanediol; 1,8-octanediol; 1,4-bis-(hydroxymethyl)-cyclohexane; 2-methylpropanediol; dipropylene glycol and dibutylene glycol, or with a polyester diol which is the reaction product of the diol with a dicarboxylic acid such as oxalic acid, malonic acid, succinic acid, adipic acid, azelaic acid and hexahydrophthalic acid or ε-caprolactone.

In addition, the carbonate diol can be also produced by a reaction of phosgene and the above-mentioned diol.

The thus obtained carbonate diol is a monocarbonate diol having one carbonate structure in one molecule thereof or a polycarbonate diol having more than one carbonate structures in one molecule thereof, and is easily available from the market as is exemplified as follows.

DESMOPHEN® 2020E (made by SUMITOMO-Bayer Co., Ltd., an average molecular weight of 2000), DN-980 (made by Nippon Polyurethane Co., Ltd., an average molecular weight of 2000), DN-981 (made by Nippon Polyurethane Co., Ltd., an average molecular weight of 1000), DN-982 (made by Nippon Polyurethane Co., Ltd., an average molecular weight of 2000), DN-983 (made by Nippon Polyurethane Co., Ltd., an average molecular weight of 1000).

Of these commercialized carbonate diols, DN-982 and DN-983 are particularly preferable for producing the addition compound (a).

DN-982, DN-983 and the like are the carbonate diols obtained by the ester exchange reaction between a carbonate derivative and a diol obtained by adding ε-caprolactone to 1,6-hexanediol. The production of the addition compound (a) of a carbonate diol and ε-caprolactone is carried out, for instance, as follows.

It is preferable in the reaction of a carbonate diol and ε-caprolactone to use an effective amount of a catalyst, namely, 0.001 to 1.0% by weight, in particular, 0.01 to 0.2% by weight of the amount of ε-caprolactone. As the catalyst, for instance, organic titanium compound such as tetraisopropyl titanate and tetrabutyl titanate and organic tin compound such as tetraphenyl tin, tetraoctyl tin, dilauryltin oxide and di-n-butyltin dichloride may be mentioned. The reaction of carbonate diol and ε-caprolactone is carried out preferably at a temperature of 50° to 300° C., in particular preferably 110° to 200° C. for a sufficient time period for completing the reaction. The amount of ε-caprolactone introduced into the reactor is preferably about one to ten mols to one mol of carbonate diol introduced into the reactor, in particular, it is preferable to use one to five mols of ε-caprolactone to one mol of carbonate diol. In order to minimize the oxidative side reaction, it is preferable to carry out the reaction under an atmosphere of inert gas such as nitrogen and the like.

The reaction product comprising the addition compound (a) may be used as it is in the next reaction.

In the di-(meth)acrylic acid ester of the present invention, the mean amount of addition of ε-caprolactone to one mol of carbonate diol is preferably 1–10 mols, more preferably 1–5 mols.

The di-(meth)acrylic acid ester of carbonate diol having an average molecular weight of 500 to 3000 (hereinafter referred to as "carbonate diol di-(meth)acrylate") can be obtained by reacting carbonate diol and (meth)acrylic acid.

The concrete production of the carbonate diol di-(meth)acrylate may be carried out while following the known process, for instance, as follows.

After adding a preferred amount of 1.0 to 2.0 mols (particularly preferable of 1.0 to 1.5 mols) of (meth)acrylic acid, a preferred amount of 0.01 to 5% by weight [based on the amount of (meth)acrylic acid] of an esterifying catalyst, for instance, p-toluenesulfonic acid, sulfuric acid and methanesulfonic acid and a preferred amount of 0.01 to 5% by weight [based on the amount of (meth) acrylic acid] of a polymerization-prohibiting agent such as methoquinone, phenothiazine and hydroquinone to 0.5 mol of carbonate diol, the thus formed mixture is heated to a preferable temperature of 70° to 130° C., and after dehydrating, the reaction mixture is washed with an alkali and water and then low-boiling substances are removed from the thus treated reaction mixture to obtain the carbonate diol di-(meth)acrylate.

The carbonate diol which is described before can be used as the starting material for producing the carbonate diol di-(meth)acrylate. Among the carbonate diol described before, DN-982 and DN-983 are particularly preferable as the starting material.

Of the carbonate diol di-(meth)acrylates, those preferable are the novel di-(meth)acrylic acid ester represented by the formula (I), and they can be produced as follows.

Namely, di-(meth)acrylic acid ester represented by the formula (I) can be produced by reacting at an elevated temperature a carbonate diol (obtained by the ester exchange reaction between an addition compound of ε-caprolactone with the diol compound and diaryl carbonate or dialkyl carbonate) represented by the following formula (II):

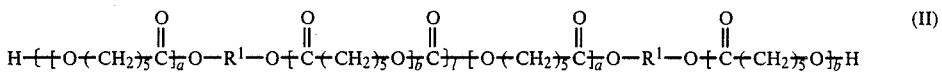

wherein $R^1$, a, b and l are defined as the above, with acrylic acid or methacrylic acid.

As a concrete example of the diol compound which is the starting material of the compound represented by the formula (II), 1,4-butanediol; 1,5-pentanediol; 1,6-hexanediol; 1,8-octanediol and hexylene glycol may be mentioned. The reaction between the diol compound and ε-caprolactone can be carried out easily at a temperature of 50° to 300° C. while using an effective amount of a catalyst, for instance, stannous chloride and tetra-isopropyl titanate. A preferred amount of the catalyst is 0.001 to 1.0% by weight of the amount of ε-caprolactone.

As a concrete example of the diaryl carbonate or dialkyl carbonate used as the raw material, for instance, diphenyl carbonate, bis-chlorophenyl carbonate, dinaphthyl carbonate, phenyl tolyl carbonate, phenyl chlorophenyl carbonate, 2,4-ditolyl carbonate, dimethyl carbonate and diethyl carbonate may be mentioned.

The ester exchange reaction between the addition compound of diol compound with ε-caprolactone and diaryl carbonate or dialkyl carbonate is carried out under a reduced pressure at a temperature of 50° to 200° C. while distilling the by-produced phenol out of the reaction system. It is preferable to use an ester exchanging catalyst, for instance, tetrabutyl titanate and sodium phenolate in an amount of 0.01 to 1% by weight of the diaryl carbonate or dialkyl carbonate.

The thus obtained carbonate diol represented by the formula (II) is monocarbonate diol having one carbonate structure in one molecule thereof or polycarbonate diol having more than one carbonate structures, and both can be easily available in the market. For example, DN-982, the compound of which has the structure containing the diol unit which is obtained by the reaction of one mol of 1,6-hexanediol and 0.83 mol (in average) of ε-caprolactone, and DN-983 the compound of which has the structure containing the diol unit which is obtained by the reaction of one mol of 1,6-hexanediol and 0.71mol (in average) of ε-caprolactone, are the examples of the carboante diol.

Di-(meth)acrylic acid ester represented by the formula (I) is produced by reacting carbonate diol represented by the formula (II) with acrylic acid, methacrylic acid or a mixture thereof. The amount of acrylic acid or methacrylic acid used in the reaction is about one to five mol to 0.5 mol of the introduced amount of carbonate diol represented by the formula (II). The reaction is preferably carried out in the presence of a polymerization inhibitor for minimizing or retarding the polymerization of the acrylic double bond. The polymerization inhibitor has been well known among the skilled persons in the art, and the polymerization inhibitor is used preferably in an amount of 0.01 to 5% by weight of the reaction mixture. As the example of the polymerization inhibitor, hydroquinone, p-methoxyphenol, 2,4-dimethyl-6-t-butylphenol, p-benzoquinone, phenothiazine, N-nitrosodiphenylamine, thiourea and copper salts may be mentioned. The above-mentioned reaction is carried out generally at a temperature of about 50° to 130° C., preferably 65° to 90° C. for a sufficient time period in order to complete the esterification of the carbonate diol represented by the formula (II) for the production of the di-(meth)acrylic acid ester represented by the formula (I) by acrylic acid or methacrylic acid. The sufficient reaction time depends on the scale of one batch, the respective reactants, the catalyst and the reaction conditions adopted. In addition, an esterification catalyst is used in an amount of preferably 0.1 to 15 mol %, more preferably 1 to 6 mol % of the amount of acrylic acid or methacrylic acid used in the esterification. Any known catalyst for esterification may be used, and as an example thereof, p-toluenesulfonic acid, methanesulfonic acid, sulfuric acid and phosphoric acid may be mentioned.

It is preferable that an inert solvent such as hexane, cyclohexane, benzene, toluene and the like exist in the reaction system, thereby removing water formed during the esterification.

In the resin composition and the coating agent of optical glass fibers according to the present invention, diacrylic acid ester is preferred to dimethacrylic acid ester as the component (A).

As the monoethylenically unsaturated monomer (B) in the present invention, various monoacrylates and monomethacrylates etc. can be used. It is preferable to use the monomeric ester which forms homopolymers of low glass transition temperature. As the concrete examples, phenyloxy (or alkylphenyloxy) polyethoxy(meth)acrylate; phenyloxy (or alkylphenyloxy) polypropoxy(meth)acrylate; nonylphenyloxy polyethoxy(meth)acrylate; phenyloxy (or alkylphenyloxy) ethoxy(meth)acrylate; phenyloxy (or alkylphenyloxy) propoxy(meth)acrylate; polyethoxy(meth)acrylate of tetrahydrofurfuryl alcohol; (meth)acrylate of an addition compound of tetrahydrofurfuryl alcohol and ε-caprolactone (made by Nippon KAYAKU Co., Ltd., KAYARAD TC-110S and TC-120 etc.); addition product of ε-caprolactone and β-hydroxyethyl (meth)acrylate (made by DAICEL Chem. Ind. Co., Ltd., PLACCEL FA-1 and FM-1 etc.); carbitol acrylate and (meth)acrylate of an addition compound of ε-caprolactone with polyethoxy- or polypropoxy compound of a phenol derivative disclosed in European Patent Publication No. 0171654 may be mentioned.

Among the monoethylenically unsaturated monomers, as the particularly preferable one, alkylphenyl polyethoxy(meth)acrylate; (meth)acrylate of an addition compound of ε-caprolactone and tetrahydrofurfuryl alcohol (made by Nippon KAYAKU Co., Ltd.,KAYARAD TC-110S and TC-120 etc.) and (meth)acrylate of an addition compound of ε-caprolactone with the polyethoxy- or polypropoxy compound of the phenol derivative disclosed in European Patent Publication No. 0171654 and represented by the following formula:

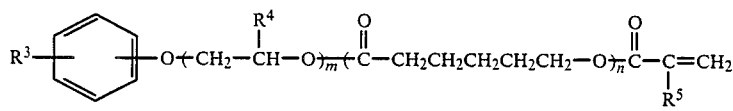

wherein $R^3$ represents a hydrogen atom or an alkyl group having 1 to 12 carbon atoms; $R^4$ and $R^5$ represent respectively a hydrogen atom or a methyl group, the mean value of m is 1 to 10 and the mean value of n is 1 to 10.

The above-mentioned compound can be obtained by reacting (meth)acrylic acid with a compound obtained by reacting ε-caprolactone to an addition compound of ethylene oxide or propylene oxide with a phenol derivative such as phenol and nonylphenol in the presence of an esterifying catalyst such as p-toluenesulfonic acid and a polymerization inhibitor such as hydroquinone at a temperature of 70° to 130° C.

As the initiator of photopolymerization (C) for use according to the present invention, although any one of the known initiator of photopolymerization may be used, it is preferred that the stability in storage after compounding is good. As such an initiator, for instance, benzoin alkyl ethers such as benzoin ethyl ether, benzoin isobutyl ether and benzoin isopropyl ether, acetophenones such as 2,2-diethoxyacetophenone and 4'-phenoxy-2,2-dichloroacetophenone, propiophenones such as 2-hydroxy-2-methylpropiophenone, 4'-isopropyl-2-hydroxy-2-methylpropiophenone and 4'-dodecyl-2-hydroxy-2-methylpropiophenone, benzyl dimethylketal, 1-hydroxycyclohexyl phenyl ketone, anthraquinones such as 2-ethylanthraquinone and 2-chloroanthraquinone and thioxanthones may be mentioned. As the particularly preferable initiator, 1-hydroxycyclohexyl phenyl ketone and benzyl dimethyl ketal etc. are mentioned. The initiator of photopolymerization may be used singly or in combination in an optional ratio.

In the resin composition (1a) and the coating agent (2a), di-(meth)acrylic acid ester (A) is preferably used in an amount in the range of 5 to 80% by weight, more preferably in the range of 20 to 70% by weight of the composition or agent. The amount of the monoethylenically unsaturated monomer (B) used in the resin composition (1a) and the coating agent (2a) is preferably in the range of 20 to 80% by weight, particularly preferably in the range of 30 to 60% by weight of the composition or agent.

On the other hand, the amount of the initiator of photopolymerization (C) used in the resin composition (1a) is generally preferable in the range of 0 to 10% by weight, of the composition, and that used in the coating agent (2a) is preferably in the range of 0.1 to 10% by weight, and particularly preferably in the range of 1 to 5% by weight of the agent.

In the resin composition (1b) and the coating agent (2b), the amount of di-(meth)acrylic acid ester (A) is preferably in the range of 5 to 50% by weight, particularly preferably in the range of 10 to 40% by weight of the composition or agent. The amount of the monoethylenically unsaturated monomer (B) used in the resin composition (1) and the coating agent (2b) is preferably in the range of 20 to 70% by weight, and particularly preferably in the range of 30 to 60% by weight of the composition or agent. The amount of the initiator of polymerization (C) used in the resin composition (1b) is preferably in the range of 0 to 10% by weight of the composition, and that used in the coating agent (2b) is preferably in the range of 0.1 to 10% by weight, and particularly preferably in the range of 1 to 5% by weight of the agent.

The average molecular weight of polyurethane (meth)acrylate (D) used in the resin composition (1b) and the coating agent (2b) is preferably higher than 1000, more preferably in the range of 2000 to 10000. As such a polyurethane (meth)acrylate, the polyurethane (meth)acrylate of polyether polyol having ether group within the molecule thereof, the polyurethane (meth)acrylate of polyester polyol having ester group within the molecule thereof, polyurethane (meth)acrylate having both the ether group and ester group and the polyurethane (meth)acrylate of carbonate diol having carbonate group within the molecule thereof may be mentioned.

As polyether polyol, for instance, polypropylene glycol, polyethylene glycol, polytetramethylene glycol and a compound formed by adding ethylene oxide or propylene oxide and the like to 1,3- and 1,4-butylene glycol, 1,6-hexanediol, neopentyl glycol, cyclohexanedimethanol, 2,2-bis(4-hydroxycyclohexyl)propane or bisphenol A may be used. The polyester polyol can be obtained by reacting an alcoholic component with an acidic component. For instance, while using a compound such as polypropylene glycol, polyethylene glycol, polytetramethylene glycol or a compound formed by adding ethylene oxide or propylene oxide and the like to 1,3- and 1,4-butylene glycol, 1,6-hexanediol, neopentyl glycol, cyclohexane dimethanol, 2,2-bis(4-hydroxycyclohexyl)propane or bisphenol A or an addition compounds formed by adding ε-caprolactone to the above compounds as the alcoholic component, a dibasic acid such as adipic acid, sebacic acid, azelaic acid and dodecanedicarboxylic acid and its anhydride is used as the acidic component. On the other hand, the compound obtained by reacting the three components, i.e., the acidic component, the alcoholic component and ε-caprolactone simultaneously is also usable as the polyester polyol. In addition, as the carbonate diol, the carbonate diol which has been used as the starting material for producing the component (A) may be used.

In order to obtain polyurethane (meth)acrylate (D) by using polyether polyol, polyester polyol or carbonate diol, an organic diisocyanate and a polymerizable monomer having hydroxyl group are reacted with hydroxyl group of polyol until substantially no isocyanate group (NCO) is contained in the reaction mixture.

As the representative organic diisocyanate, aromatic diisocyanate such as tolylenediisocyanate and 4,4'-diphenylmethanediisocyanate, cycloaliphatic diisocyanate such as isophorone diisocyanate and 4,4'-dicyclohexylmethanediisocyanate, aliphatic diisocyanate such as hexamethylene diisocyanate and 2,2'-trimethylhexamethylene diisocyanate may be mentioned. As the polymerizable monomer having hydroxyl group, (meth)acrylates having hydroxyl group, such as β-hydroxyethyl (meth)acrylate, β-hydroxypropyl (meth)acrylate, β-hydroxylauryl (meth)acrylate and an addition compound of ε-caprolactone and β-hydroxyethyl (meth)acrylate may be mentioned.

Such a reaction of the isocyanate group and the hydroxyl group proceeds without any catalyst, however, a customary catalyst, for instance, tertiary amine such as triethylamine, organic metal compound such as dibutyltin dilaurate and dibutyltin diacetate or tin chloride may be used.

As the particularly preferable polyurethane (meth)acrylate (D), polyurethane acrylate of carbonate diol may be mentioned, and as the particularly preferable organic diisocyanate, isophorone diisocyanate and 4,4'-dicyclohexylmethane diisocyanate may be mentioned.

The amount of polyurethane (meth)acrylate (D) used according to the present invention is preferably 20 to 70% by weight of the resin composition (1b) or the coating agent (2b), and more preferably 40 to 60% by weight. The larger amount may make the viscosity of the composition higher.

The resin composition and coating agent according to the present invention may be used, according to the necessity, after further adding thereinto epoxyacrylate, polyester acrylate and polyurethane acrylate, for instance, polyurethane acrylate of polyol having ether group, ester group or carbonate group in the molecule thereof, or polymerizable monomer, for instance, polyethylene glycol di-(meth)acrylate, polypropylene glycol di-(meth)acrylate, trimethylolpropane tri-(meth)acrylate and the like.

In addition, resin for denaturation and various additives may be added to the resin composition and coating agent of the present invention, and as the resin for denaturation, epoxy resin, polyurethane, polybutadiene, polyether, polyamide imide, silicone resin and phenol resin may be mentioned. On the other hand, as the additives, organic silicon compounds, surfactants and polymerization inhibitor may be mentioned.

The resin composition according to the present invention is useful for coating optical glass fibers and may be used as an adhesive agent for laminate glass plates and an agent for treating fibers.

In the case where optical glass fibers are coated, the di-coating method is suitably adopted. In such a case, coating can be carried out at a very large speed of 3 to 7 m/sec. The thickness of the agent coated on the optical glass fiber is not particularly limited, however, it is preferably 20 to 300 μm in ordinary cases.

The coating agent according to the present invention is easily cured by irradiation of ultraviolet rays, and the curing of the coating agent of the present invention can be carried out by an ordinary method by irradiating ultraviolet rays from, for instance, low pressure- or high pressure mercury lamp or xenon lamp.

Although di-(meth)acrylic acid ester represented by the formula (I) is useful as a component of the coating agent of optical glass fibers, it is also useful as the vehicle of various coating compositions and ink composition, and the compositions containing di-(meth)acrylic acid ester represented by the formula (I) can be cured by radiation or by thermal means. The radiation curing can be carried out by particle radiation of electron beam or ionization, or chemical beam such as ultraviolet rays.

In the case where curing is carried out by chemical beam, an initiator of photopolymerization, for instance, benzophenone, ethyl N,N-dimethylbenzoate and the aforementioned compounds, is mixed with the starting material.

The curing technique by radiation or heat has been well known by the person skilled in the art, and the curing in the present invention can be carried out by the technique.

The di-(meth)acrylic acid ester represented by the formula (I) is used singly or after being mixed with other monomeric compound, for instance, trimethylolpropane triacrylate, pentaerythritol triacrylate and pentaerythritol tetraacrylate, or a resin containing unsaturated groups, for instance, unsaturated polyester, polyester acrylate, epoxy acrylate and urethane acrylate, as a vehicle. In the case of using the di-(meth)acrylic acid ester while mixing with other monomer or a resin, the mixing ratio may be optional and is not particularly limited.

The novel di-(meth)acrylic acid ester represented by the formula (I) can be polymerized also by the addition of an organic peroxide, for instance, benzoyl peroxide, methyl ethyl ketone peroxide, cumene hydroperoxide and the like.

The present invention will be explained concretely while referring to the following non-limiting examples, wherein the term "part" means "part by weight".

EXAMPLE A 1

Into a 2-liter reaction vessel provided with a stirrer, a temperature controller, a thermometer, a condenser and a separator, 700 parts of the compound of the following formula:

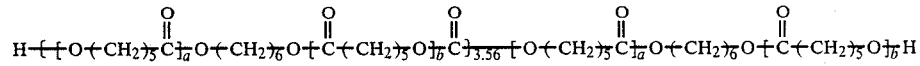

wherein the mean sum of a plus b is 0.71 (made by Nippon Polyurethane Co., Ltd., DN-983, an OH value of 112.2 mgKOH/g, an average molecular weight of about 1000 and a melting point of 5° C.), 121 parts of acrylic acid, 14 parts of p-toluenesulfonic acid, 1.0 part of hydroquinone, 560 parts of benzene and 140 parts of cyclohexane were introduced, and the thus introduced substances were heated to a reaction temperature of 80° to 86° C. while distillating the water formed in the reaction together with the solvent, removing the water from the reaction system by the separator and returning only the solvent to the reaction vessel. The reaction was carried out until 25.2 parts of water were removed. The thus obtained reaction mixture was dissolved in a mixture of 960 parts of benzene and 240 parts of cyclohexane, and after neutralizing the solution with an aqueous 20% solution of sodium hydroxide, the neutralized solution was washed three times with each 500 parts of an aqueous 20% solution of sodium chloride. By distilling the solvent from the thus treated solution, 690 parts of pale yellow liquid having the following properties were obtained:

| | |
|---|---|
| Specific gravity (at 25° C.) | 1.1000 |
| Viscosity (at 25° C.) | 2100 centripoises |
| Saponification value | 414.4 mgKOH/g |
| Acid value | 0.01 mgKOH/g and |
| Refractive index (at 20° C.) | 1.4680 |

The result of determination of the absorption frequencies of the thus obtained product by nuclear magnetic resonance (NMR) of a high resolving power is shown below.

| No. | Frequency (Hz) | No. | Frequency (Hz) |
|---|---|---|---|
| 1 | 2603.515 | 10 | 966.796 |
| 2 | 2495.140 | 11 | 962.890 |
| 3 | 2333.984 | 12 | 935.546 |
| 4 | 1958.984 | 13 | 511.718 |
| 5 | 1933.593 | 14 | 490.234 |
| 6 | 1199.218 | 15 | 429.687 |
| 7 | 1166.015 | 16 | 382.812 |
| 8 | 1134.865 | 17 | 369.140 |
| 9 | 1015.625 | 18 | 0.000 |

In the determination, tetramethylsilane was used as the standard substance, chloroform was used as a solvent, and the determination was conducted first by $^1$H and $^{13}$C-H coupling and finally by $^{13}$C-D coupling to obtain identification results. The absorption peaks of Nos. 6, 7 and 8 are those by the solvent, and that of No. 18 shows the position of the peak of tetramethylsilane.

EXAMPLE A 2

Into the same reaction vessel as in Example 1, 700 parts of a compound represented by the following formula:

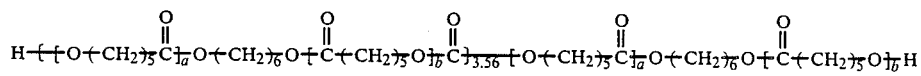

wherein the mean sum of a plus b is 0.83 (made by Nippon Polyurethane Co., Ltd., DN-982, an OH value of 56 mgKOH/g, the average molecular weight of about 2000 and a melting point of 5° C.), 61 parts of acrylic acid, 6 parts of p-toluenesulfonic acid, 0.4 part of hydroquinone, 560 parts of benzene and 140 parts of cyclohexane were introduced, and the reaction was carried out as in Example A 1 until the amount of the thus formed water became 12.6 parts at a reaction temperature of 81° to 86° C. After dissolving the reaction mixture in a mixture of 1200 parts of benzene and 300 parts of cyclohexane, the solution was neutralized, washed and subjected to de-solvent as in Example A 1 to obtain 654 parts of a pale yellow liquid of the following properties.

| Specific gravity (at 25° C.) | 1.1060 |
|---|---|
| Viscosity (at 25° C.) | 13750 centipoise |
| Saponification value | 415.7 mgKOH/g |
| Acid value | 0.03 mgKOH/g and |
| Refractive index (at 20° C.) | 1.4700 |

The result of determination of NMR is as follows:

| No. of Peak | Frequency (Hz) | No. of Peak | Frequency (Hz) |
|---|---|---|---|
| 1 | 2607.421 | 8 | 1017.578 |
| 2 | 2333.987 | 9 | 964.843 |
| 3 | 1960.937 | 10 | 511.718 |
| 4 | 1933.593 | 11 | 429.687 |
| 5 | 1195.312 | 12 | 382.812 |
| 6 | 1164.062 | 13 | 369.140 |
| 7 | 1130.859 | 14 | 0.000 |

Of the above-mentioned peaks, those of Nos. 5, 6 and 7 are the positions of the absorption peaks of the solvent, and that of No. 14 is that of tetramethylsilane.

EXAMPLE A 3

Into the same reaction vessel as in Example A 1, 700 parts of a compound represented by the following formula:

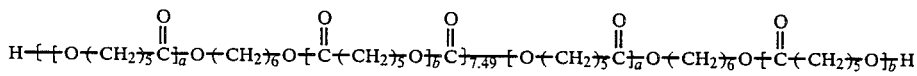

wherein the mean sum of a plus b is 0.71 (made by Nippon Polyurethane Co., Ltd., DN-983, an OH value of 112.2 mgKOH/g, the average molecular weight of about 1000 and the melting point of 5° C.), 145 parts of methacrylic acid, 4.5 parts of sulfuric acid, 1.1 parts of hydroquinone and 700 parts of toluene were introduced, and the reaction was carried out as in Example A 1 at a temperature of 105° to 116° C. until the amount of the thus formed water became 25.2 parts. After dissolving the reaction mixture in 1000 parts of toluene, the solution was neutralized, washed and subjected to de-solvent as in Example A 1 to obtain 723 parts of a pale yellow liquid of the following properties:

| Specific gravity (at 25° C.) | 1.0940 |
|---|---|
| Viscosity (at 25° C.) | 1900 centipoises |
| Saponification value | 400.0 mgKOH/g |
| Acid value | 0.02 mgKOH/g and |
| Refractive index (at 20° C.) | 1.4680 |

The result of NMR determination is shown below:

| No. of Peak | Frequency (Hz) | No. of Peak | Frequency (Hz) |
|---|---|---|---|
| 1 | 2601.562 | 10 | 968.750 |
| 2 | 2509.765 | 11 | 962.890 |
| 3 | 2333.984 | 12 | 933.593 |
| 4 | 2052.734 | 13 | 509.765 |
| 5 | 1878.906 | 14 | 429.687 |
| 6 | 1201.171 | 15 | 382.812 |
| 7 | 1167.968 | 16 | 369.140 |
| 8 | 1136.718 | 17 | 273.437 |
| 9 | 1015.625 | 18 | 0.000 |

Of the above-mentioned absorption peaks, those of Nos. 6, 7 and 8 are those of the solvent, and that of No. 18 is that of tetramethylsilane.

The following Production Example A series are the examples of the production of the addition compound (a) obtained by the reaction of a carbonate diol and ε-caprolactone.

PRODUCTION EXAMPLE A 1

Into a 3-liter reaction vessel provided with a stirrer, a temperature controller, a thermometer and a condenser, 2000 parts of a carbonate diol (made by Nippon Polyurethane Co., Ltd., DN-982, an OH value of 56 mgKOH/g, an average molecular weight of about 2000 and a melting point of 5° C.), 342 parts of ε-caprolactone (made by DAICEL Chem. Ind. Co., Ltd., PLACCEL®M) and 0.17 part of stannous chloride were introduced, and the thus introduced mixture was heated to 130° to 150° C. under nitrogen gas atmosphere until the amount of unreacted ε-caprolactone became less than 1% by weight. The thus obtained addition compound (a-1) was a pale yellow liquid of an OH group value of 47.9 and an acid value of 1.1. As a result of determination of the molecular weight of the product, the present addition compound (a-1) of the carbonate diol and ε-caprolactone had, in average, about three molecular units of ε-caprolactone in one molecule of the addition compound.

PRODUCTION EXAMPLE A 2

Into the same reaction vessel as in Production Example A 1, 2000 parts of the same carbonate diol as that used in Production Example A 1, 798 parts of the same ε-caprolactone as that used in Production Example A 1 and 0.4 part of stannous chloride were introduced, and the thus obtained mixture was reacted under gaseous nitrogen atmosphere at a temperature of 130° to 150° C. until the amount of the unreacted ε-caprolactone became less than 1% by weight. The thus obtained addition compound (a-2) was a pale yellow liquid of an OH value of 40.1 and an acid value of 1.5. As a result of determination of the molecular weight of the product, it was found that the addition compound (a-2) of the carbonate diol and ε-caprolactone had, in average, about seven molecular units of ε-caprolactone in the molecule of the addition compound.

PRODUCTION EXAMPLE A 3

In the same reaction vessel as in Production Example A 1, 1000 parts of the same carbonate diol (DN-983) as that used in Example A 3, 224 parts of ε-caprolactone and 0.12 part of tetra-isopropyl titanate were introduced, and the thus obtained mixture was reacted at a temperature of 150° to 160° C. under nitrogen gas atmosphere until the amount of the unreacted ε-caprolactone became less than 1% by weight. The thus obtained addition compound (a-3) was a pale yellow liquid of an OH value of 91.3 and an acid value of 2.1.

As a result of determination of the molecular weight of the product, it was found that the addition compound (a-3) had, in average, two molecular units of ε-caprolactone in one molecule of the addition compound.

PRODUCTION EXAMPLE A 4

In the same reaction vessel as that used in Production Example A 1, 1014.6 parts of a carbonate diol (made by Nippon Polyurethane Co., Ltd., DN-981, an OH value of 110 mgKOH/g and an average molecular weight of about 1000 and a melting point of 43° C.), 456 parts of ε-caprolactone and 0.23 part of stannous chloride were introduced, and the thus obtained mixture was reacted at a temperature of 130° to 150° C. under nitrogen gas atmosphere. The thus obtained addition compound (a-4) was a pale yellow liquid of an OH value of 76.3 and an acid value of 1.3. As a result of determination of the molecular weight of the addition compound thus obtained, it was found that the addition compound (a-4) had, in average, about 4 molecular units of ε-caprolactone in one molecule of the addition compound (a-4).

The following examples B series are the examples of producing the di-(meth)acrylic acid ester.

EXAMPLE B 1

Into a 2-liter reaction vessel provided with a stirrer, a temperature controller, a thermometer and a condenser, 749.4 parts of the addition compound (a-1) which had been obtained in Production Example A 1, 55.4 parts of acrylic acid, 6.4 parts of p-toluenesulfonic acid, 0.5 part of hydroquinone, 588.8 parts of benzene and 147.2 parts of cyclohexane were introduced, the reaction was carried out at a temperature of 81° to 87° C. in the similar manner as in Example A 1 until 11.5 parts of water were removed. After dissolving the reaction mixture in a mixture of 960 parts of benzene and 240 parts of cyclohexane, the solution was neutralized by an aqueous 20% solution of sodium hydroxide and washed three times with each 500 parts of an aqueous 20% solution of sodium chloride. By distilling the solvents from the thus treated solution, 678 parts of a pale yellow liquid of the following properties were obtained.

| | |
|---|---|
| Specific gravity (at 25° C.) | 1.1040 |
| Viscosity (at 25° C.) | 15000 centipoise |
| Saponification value | 422.7 mgKOH/g |
| Acid value | 0.03 mgKOH/g and |
| Refractive index (at 20° C.) | 1.4700 |

As a result of NMR determination of the thus obtained ester the following data were obtained.

| No. of Peak | Frequency (Hz) | No. of Peak | Frequency (Hz) |
|---|---|---|---|
| 1 | 2605.468 | 9 | 962.890 |
| 2 | 2333.984 | 10 | 937.500 |
| 3 | 1960.937 | 11 | 511.718 |
| 4 | 1935.546 | 12 | 429.687 |
| 5 | 1199.218 | 13 | 382.812 |
| 6 | 1166.015 | 14 | 369.140 |
| 7 | 1134.705 | 15 | 0.000 |
| 8 | 1017.578 | | |

The data were arranged in the same manner as in Example A 1, and the peaks of Nos. 5, 6 and 7 are those of the solvent and that of No. 15 is that of tetramethylsilane.

EXAMPLE B 2

In the same reaction vessel as in Example B 1, 727.4 parts of the addition compound (a - 2) which had been obtained in Production Example A 2, 45 parts of acrylic acid, 5.2 parts of p-toluenesulfonic acid, 0.34 part of hydroquinone, 582.4 parts of benzene and 145.6 parts of cyclohexane were introduced, and the thus obtained mixture was reacted in the same manner as in Example A 1 at a reaction temperature of 81° to 86° C. until 9.3 parts of water were removed.

After dissolving the reaction mixture in a mixture of 1200 parts of benzene and 300 parts of cyclohexane, the thus formed solution was neutralized, washed and subjected to de-solvent in a similar manner as in Example A 1 thereby obtaining 657 parts of a pale yellow liquid of the following properties.

| | |
|---|---|
| Specific gravity (at 25° C.) | 1.1030 |
| Viscosity (at 25° C.) | 18000 centipoise |
| Saponification value | 424 mgKOH/g |
| Acid value | 0.05 mgKOH/g and |

-continued

| Refractive index (at 20° C.) | 1.4720 |
|---|---|

The result of NMR determination of the thus obtained ester is shown below.

| No. of Peak | Frequency (Hz) | No. of Peak | Frequency (Hz) |
|---|---|---|---|
| 1 | 2603.515 | 9 | 962.890 |
| 2 | 2333.984 | 10 | 935.546 |
| 3 | 1960.937 | 11 | 511.718 |
| 4 | 1933.593 | 12 | 490.234 |
| 5 | 1199.218 | 13 | 429.687 |
| 6 | 1166.015 | 14 | 382.812 |
| 7 | 1134.765 | 15 | 369.140 |
| 8 | 1017.578 | 16 | 0.000 |

Of the above-mentioned peaks, those of Nos. 5, 6 and 7 are those of the absorption peaks of the solvent, and that of No. 16 is that of tetramethylsilane.

EXAMPLE B 3

In the same reaction vessel as in Example B 1, 708.4 parts of the addition compound (a-4) obtained in Production Example A 4, 72.6 parts of acrylic acid, 9.6 parts of p-toluenesulfonic acid, 0.5 part of hydroquinone, 576 parts of benzene and 144 parts of cyclohexane were introduced, and the thus obtained mixture was reacted in the same manner as in Example B 1 until the amount of the removed water became 17.2 parts. After dissolving the reaction mixture in a mixture of 1200 parts of benzene and 300 parts of cyclohexane, the thus formed solution was subjected to neutralization, washing and de-solvent in the same manner as in Example B 1 to obtain 654 parts of a pale yellow liquid of the following properties.

| Specific gravity (at 25° C.): | 1.1020 |
|---|---|
| Viscosity (at 25° C.): | 5000 centipoise |
| Saponification value: | 419.8 mgKOH/g |
| Acid value: | 0.03 mgKOH/g and |
| Refractive index (at 20° C.): | 1.4700 |

The result of NMR determination of the thus obtained ester is shown below.

| No. of Peak | Frequency (Hz) | No. of Peak | Frequency (Hz) |
|---|---|---|---|
| 1 | 2605.468 | 9 | 1017.578 |
| 2 | 2496.093 | 10 | 962.890 |
| 3 | 2333.984 | 11 | 511.718 |
| 4 | 1960.937 | 12 | 429.687 |
| 5 | 1933.593 | 13 | 380.859 |
| 6 | 1195.312 | 14 | 369.140 |
| 7 | 1164.062 | 15 | 0.000 |
| 8 | 1130.859 | | |

Of the above-mentioned peaks, those of Nos. 6, 7 and 8 are those of the absorption peaks of the solvent, and that of No. 15 is that of the position of the peak of tetramethylsilane.

EXAMPLE B 4

In the same reaction vessel as in Example B 1, 700 parts of the addition compound (a - 3) obtained in Production Example A 3, 98.6 parts of acrylic acid, 7.6 parts of p-toluenesulfonic acid, 0.8 part of hydroquinone, 576 parts of benzene and 144 parts of cyclohexane were introduced, and the thus obtained mixture was reacted in the same manner as in Example B 1 until the amount of the removed water became 20.5 parts. After dissolving the reaction mixture in a mixture of 1200 parts of benzene and 300 parts of cyclohexane, the solution was subjected to neutralization, washing and de-solventing to obtain 537 parts of a pale yellow liquid of the following properties.

| Specific gravity (at 25° C.): | 1.0990 |
|---|---|
| Viscosity (at 25° C.): | 2780 centipoise |
| Saponification value: | 424.3 mgKOH/g |
| Acid value: | 0.01 and |
| Refractive index (at 20° C.): | 1.4695 |

The result of determination of NMR of the thus obtained ester is shown as follows.

| No. of Peak | Frequency (Hz) | No. of Peak | Frequency (Hz) |
|---|---|---|---|
| 1 | 2605.468 | 9 | 1017.578 |
| 2 | 2494.140 | 10 | 962.890 |
| 3 | 2333.984 | 11 | 935.546 |
| 4 | 1960.937 | 12 | 511.718 |
| 5 | 1935.546 | 13 | 429.687 |
| 6 | 1199.218 | 14 | 382.812 |
| 7 | 1166.015 | 15 | 369.140 |
| 8 | 1134.764 | 16 | 0.000 |

Of the above-mentioned peaks, those of Nos. 6, 7 and 8 are the absorption peaks of the solvent, and that of No. 16 shows the position of the absorption peak of tetramethylsilane.

EXAMPLE B 5

In the same reaction vessel as in Example B 1, 749.4 parts of the addition compound (a-1) which had been obtained in Production Example A 1, 66.2 parts of methacrylic acid, 6.4 parts of p-toluenesulfonic acid, 0.5 part of hydroquinone, 588.8 parts of benzene and 147.2 parts of cyclohexane were introduced, and the thus obtained mixture was reacted in the same manner as in Example B 1 until the amount of the removed water became 11.6 parts. After dissolving the reaction mixture in a mixture of 960 parts of benzene and 240 parts of cyclohexane, the thus prepared solution was subjected to neutralization, washing and de-solventing to obtain 678 parts of a pale yellow liquid of the following properties.

| Specific gravity (at 25° C.): | 1.1000 |
|---|---|
| Viscosity (at 25° C.): | 9416 centipoise |
| Saponification value: | 409.8 mgKOH/g |
| Acid value: | 0.03 mgKOH/g and |
| Refractive index (at 20° C.): | 1.4700 |

The result of determination of NMR is shown as follows.

| No. of Peak | Frequency (Hz) | No. of Peak | Frequency (Hz) |
|---|---|---|---|
| 1 | 2605.468 | 10 | 962.890 |
| 2 | 2513.671 | 11 | 937.500 |
| 3 | 2335.937 | 12 | 511.718 |
| 4 | 2052.734 | 13 | 490.234 |
| 5 | 1880.859 | 14 | 429.687 |
| 6 | 1199.218 | 15 | 382.812 |
| 7 | 1166.015 | 16 | 369.140 |
| 8 | 1134.765 | 17 | 275.390 |
| 9 | 1017.578 | 18 | 0.000 |

Of the above-mentioned peaks, those of Nos. 6, 7 and 8 are the absorption peak of the solvent, and that of No. 18 shows the position of the absorption peak of tetramethylsilane.

The following Production Example B is an example of the production of monoacrylate of the addition compound obtained by the reaction of an addition compound obtained by reacting nonylphenol with ethyleneoxide (1:4 (mol)) and ε-caprolactone (1:2 (mol)).

PRODUCTION EXAMPLE B 1

In a 2-liter reaction vessel provided with a stirrer, a temperature controller, a thermometer and a condenser, 624 parts of a compound represented by the following formula:

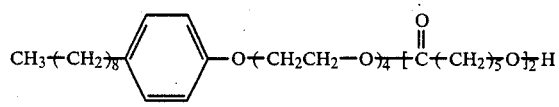

108 parts of acrylic acid, 16.8 parts of p-toluenesulfonic acid, 1.0 part of hydroquinone, 560 parts of benzene and 140 parts of cyclohexane were introduced, and the thus obtained mixture was reacted in the same manner as in Example A 1 at a temperature of 80° to 87° C. until the amount of the removed water became 18 parts. After dissolving the reaction mixture in a mixture of 1040 parts of benzene and 260 parts of cyclohexane, the thus formed solution was subjected to neutralization by an aqueous 20% solution of sodium hydroxide and then washed three times with each 500 parts of an aqueous 20% solution of sodium chloride, and the solvent of the thus washed solution was distilled off under a reduced pressure to obtain 596 parts of a pale yellow liquid of the following properties.

| | |
|---|---|
| Specific gravity (at 25° C.): | 1.045 |
| Viscosity (at 25° C.): | 68.8 centipoise |
| Saponification value: | 248 mgKOH/g and |
| Acid value: | 0.04 mgKOH/g |

The following Production Examples C are the examples for producing a polyurethane acrylate.

PRODUCTION EXAMPLE C 1

In the same reaction vessel as in Production Example B 1, 253.1 parts of polypropylene glycol of a molecular weight of about 2000 and an OH value of 56.1, 251.3 parts of polyester polyol which was the reaction product of neopentyl glycol, adipic acid and ε-caprolactone (made by DAICEL Chem. Ind. Co., Ltd., PLACCEL L-220AL, a molecular weight of about 2000 and an OH value of 57.5) and 84.7 parts of isophorone diisocyanate were introduced, and after heating the thus obtained mixture, the mixture was reacted for 10 hours at 75° C., and after cooling the reaction mixture to 60° C., 91.4 parts of an addition compound of ε-caprolactone and β-hydroxyethyl acrylate (made by DAICEL Chem. Ind. Co., Ltd., PLACCEL FA-2), 0.3 part of methoquinone and 0.12 part of di-n-butyltin dilaurate were additionally introduced into the reaction vessel, and the thus formed mixture was heated and reacted at a temperature of 75° to 80° C. to obtain a product of a viscosity of 110 poise at 60° C. and a refractive index of 1.4721 at 20° C.

PRODUCTION EXAMPLE C 2

In the same reaction vessel as in Production Example C 1, 500 parts of a carbonate diol (made by SUMITOMO-Bayer Co., Ltd., DESMOPHEN 2020E, a molecular weight of about 2000 and an OH value of 56) and 83.3 parts of isophorone diisocyanate were introduced, and after heating the content of the reaction vessel, the content was reacted at a temperature of 75° C. for 10 hours, and after cooling the reaction mixture to 60° C., 90.3 parts of the same addition compound (PLACCEL FA-2) as in Production Example C 1, 0.3 part of methoquinone and 0.1 part of di-n-butyltin dilaurate were added to the reaction mixture. The mixture was reacted at a temperature of from 75° to 80° C. The thus obtained product showed a viscosity of 675 poise at 80° C. and a refractive index of 1.4730 at 20° C.

PRODUCTION EXAMPLE C 3

In the same reaction vessel as in Production Example C 1, 432 parts of a polyester diol (made by DAICEL Chem. Ind. Co., Ltd., PLACCEL P-2203, a molecular weight of about 2000 and an OH value of 57.9) which was the reaction product of polypropylene glycol and ε-caprolactone, and 84.9 parts of 4,4'-diphenylmethane diisocyanate were introduced, and the mixture was reacted at 75° C. for 10 hours. Then, after cooling the reaction mixture to 60° C., 26.2 parts of 2-hydroxyethyl acrylate, 0.27 part of methoquinone and 0.11 part of di-n-butyltin dilaurate were added to the reaction mixture, and the mixture was brought into reaction at a temperature of 75° to 80° C. The thus obtained product showed a viscosity of 88 poise at 80° C. and a refractive index of 1.4920 at 20° C.

The following series of Examples C are the examples of preparing the resin composition curable by ultraviolet rays.

EXAMPLE C 1

A resin composition C-A was prepared by mixing 70 parts of diacrylic acid ester obtained in Example B 1, 30 parts of monoacrylate of an addition compound of 2 mols of ε-caprolactone and one mol of an addition compound of one mol of nonylphenol and 4 mols of ethylene oxide, 5 parts of 1-hydroxycyclohexyl phenyl ketone (made by Ciba-Geigy Co., Ltd., ILGACURE-184) and 0.01 part of methylhydroquinone. The properties of the resin composition C-A and that of the cured product of the resin composition C-A are shown in Table 1.

EXAMPLE C 2

A resin composition C-B was prepared by mixing 50 parts of diacrylic acid ester obtained in Example B 2, 50 parts of monoacrylate of an addition cmmpound of one mol of nonylphenol and seven mols of ethylene oxide, 5 parts of 4'-dodecyl-2-hydroxy-2-methylpropiophenone (made by Merck Co., Ltd., DAROCURE-953) and 0.01 part of methylhydroquinone. The property of the thus prepared resin composition and that of the cured product of the cured product of the resin composition are shown in Table 1.

EXAMPLE C 3

A resin composition C-C was prepared by mixing 20 parts of diacrylic acid ester obtained in Example B 3, 30 parts of polyurethane acrylate which had been obtained by reacting 0.5 mol of polypropylene glycol of the molecular weight of about 2000, 0.5 mol of polyester polyol (made by DAICEL Chem. Ind. Co., Ltd., PLACCEL L-220AL, a molecular weight of about 2000) and 1.5 mol of isophorone diisocyanate at 75° to 80° C. and further reacting the thus obtained reaction mixture with 1.1 mol of an addition compound of ε-caprolactone and β-hydroxyethyl acrylate (PLACCEL FA-2), 30 parts of monoacrylate of an addition compound of 1 mol of nonylphenol and 7 mols of ethylene oxide, 20 parts of monoacrylate of an addition compound of 2 mols of ε-caprolactone and one mol of another addition compound of one mol of nonylphenol and 4 mols of ethylene oxide, 5 parts of 1-hydroxycyclohexyl phenyl ketone and 0.01 part of methylhydroquinone. The property of the thus prepared resin composition and that of the cured product of the thus prepared resin composition are also shown in Table 1.

EXAMPLE C 4

A resin composition C-D was prepared by mixing 20 parts of diacrylic acid ester obtained in Example B 4, 10 parts of dimethacrylic acid ester obtained in Example B 5, 25 parts of polyurethane acrylate used in Example C 3, 15 parts of monoacrylate of a compound obtained by reacting one mol of ε-caprolactone with one mol of tetrahydrofurfuryl alcohol (made by NIPPON KAYAKU Co., Ltd., KAYARAD TC-110S), 30 parts of monoacrylate of an addition compound of one mol of nonylphenol and 7 mols of ethylene oxide, 5 parts of 1-hydroxycyclohexyl phenyl ketone and 0.01 part of methylhydroquinone. The property of the thus prepared resin composition C-D and that of the cured product of the resin composition C-D are also shown in Table 1.

COMPARATIVE EXAMPLE A 1

For comparison, as a conventional coating composition which was curable by ultraviolet rays for use in optical fibers, a commercialized product (by Desoto Chemical Co. under the registered trade name of DESOTO 950×065 was used as a resin composition A-E. The property of the resin composition A-E and that of the cured product thereof are also shown in Table 1 for comparison.

TABLE 1

| | Resin composition | | | | |
|---|---|---|---|---|---|
| | C-A | C-B | C-C | C-D | A-E (Comparative) |
| Viscosity (cps, 25° C.) | 4950 | 4600 | 4400 | 3300 | 10000 |
| Hardness (Shore A) | 60 | 32 | 56 | 58 | 50 |
| Glass transition temperature (°C.) | −53 | −53 | −50 | −54 | −25 |
| Young's Modulus (kg/cm$^2$) at | | | | | |
| 70° C. | 30 | 12 | 27 | 30 | 25 |
| 40° C. | 30 | 12 | 27 | 30 | 25 |
| 23° C. | 30 | 12 | 27 | 30 | 25 |
| 0° C. | 30 | 12 | 27 | 30 | 91 |
| −20° C. | 30 | 12 | 27 | 30 | 105 |
| −40° C. | 30 | 12 | 27 | 30 | 166 |
| Rate of water absorption (% of increase of weight) | 0.4 | 0.8 | 1.0 | 1.1 | 29.7 |

Notes in Table 1:
Determination of Shore Hardness A (Shore A):

By exposing each of the resin compositions C-A, C-B, C-C, C-D and A-E to ultraviolet rays from a high-pressure mercury lamp (output of 2 kw) placed parallel to the resin composition and at a height of 8 cm from the resin composition, at a conveyer speed of 30 m/min, each of the sheets of cured material of 250 μm in thickness was produced and the

TABLE 1-continued hardness (Shore A) of the sheet was determined following the method of Japanese Industrial Standards (JIS)-Z2246.
Determination of Glass Transition Temperature:

Glass Transition Temperature of every specimens of the sheets prepared as in the Determination of Shore Hardness A was determined by using viscoelasticity spectrometer (made by Iwamoto Mfg. Co., Ltd.).
Young's Modulus (kg/cm$^2$):

Young's modulus of every specimens of the sheets prepared as in the Determination of Shore Hardness A was determined at one of several temperatures shown in Table 1.
Determination of Rate of Water Absorption:

The rate of water absorption of the cured resin composition was determined from the weights before and after immersion of the specimen prepared by the same method as in the Determination of Shore Hardness A in pure water at 20° C. for 24 hours. Namely the increase of the weight of the specimen by absorbing water was determined.

EXAMPLE C 5

By heating the parent material for optical glass fibers to about 2000° C., the optical glass fibers of 125 μm in outer diameter were prepared at a spinning velocity of 5 m/sec. In the successive step, each of the resin compositions C-A to C-D was coated onto the thus spun optical glass fibers by die-coating method, and the thus coated optical glass fibers were exposed to ultraviolet rays from a high pressure mercury lamp of 2 kw to cure the resin compositions on the glass fibers. No transmission loss was observed on the thus coated optical glass fibers until −60° C.

EXAMPLE D 1

A resin composition D-A was prepared by mixing 10 parts of the carbonate diol diacrylate obtained in Example A 1, 40 parts of polyurethane acrylate obtained in Production Example C 1, 40 parts of a monoacrylate of an addition compound of 2 mols of ε-caprolactone and one mol of another addition compound of one mol of nonylphenol and 4 mols of ethylene oxide, 10 parts of monoacrylate of a compound obtained by reacting one mol of ε-caprolactone with one mol of tetrahydrofurfuryl alcohol (made by NIPPON KAYAKU Co., Ltd., KAYARAD TC-110S), 5 parts of 1-hydroxycyclohexyl phenyl ketone (refer to Example C 1), and 0.01 part of methylhydroquinone. The properties of the thus prepared resin composition D-A and the cured material thereof are shown in Table 2.

EXAMPLE D 2

A resin composition D-B was prepared by mixing 40 parts of the carbonate diol diacrylate obtained in Example A 2, 25 parts of polyurethane acrylate obtained in Production Example C 1, 25 parts of monoacrylate of an addition compound of 2 mols of ε-caprolactone and one mol of another addition compound of one mol of nonylphenol and 4 mols of ethylene oxide, 5 parts of 1-hydroxycyclohexyl phenyl ketone (refer to Example C 1) and 0.01 part of methylhydroquinone. The physical property of the resin composition D-B and the cured product thereof is shown also in Table 2.

EXAMPLE D 3

A resin composition D-C was prepared by mixing 20 parts of the carbonate diol diacrylate obtained in Example A 2, 20 parts of polyurethane acrylate obtained in Production Example C 2, 40 parts of monoacrylate of an addition compound of 2 mols of ε-caprolactone and one mol of another addition compound of one mol of nonylphenol and 4 mols of ethylene oxide, 20 parts of monoacrylate of an addition compound of one mol of nonylphenol and 7 mols of ethylene oxide, 5 parts of 4'-dodecyl-2-hydroxy-2-methyl-propiophenone (made by Merck Co., Ltd., DAROCURE-953) and 0.01 part of methylhydroquinone. The physical property of the thus prepared resin composition D-C and the cured product thereof is also shown in Table 2.

EXAMPLE D 4

A resin composition D-D was prepared by mixing 10 parts of the carbonate diol dimethacrylate obtained in Example A 3, 10 parts of the carbonate diol diacrylate obtained in Example A 2, 30 parts of polyurethane acrylate obtained in Production Example C 3, 10 parts of phenoxyethyl acrylate, 40 parts of monoacrylate of an addition compound of one mol of nonyl phenol and 7 mols of ethylene oxide, 5 parts of ILGACURE-184 (refer to Example C 1) and 0.01 part of methylhydroquinone. The physical property of the thus prepared resin composition D-D and the cured product thereof is also shown in Table 2.

TABLE 2

| | Resin composition | | | | |
|---|---|---|---|---|---|
| | D-A | D-B | D-C | D-D | A-E*[1] |
| Viscosity (cps, 25° C.) | 7000 | 7600 | 5300 | 4100 | 10000 |
| Hardness (Shore A) | 57 | 51 | 53 | 50 | 50 |
| Glass transition temperature (°C.) | −50 | −44 | −49 | −40 | −25 |
| Young's Modulus (kg/cm$^2$) at | | | | | |
| 70° C. | 32 | 24 | 25 | 21 | 25 |
| 40° C. | 32 | 24 | 25 | 21 | 25 |
| 23° C. | 32 | 24 | 25 | 21 | 25 |
| 0° C. | 32 | 24 | 25 | 21 | 91 |
| −20° C. | 32 | 24 | 25 | 21 | 105 |
| −40° C. | 36 | 26 | 26 | 24 | 166 |
| Rate of water absorption (%) | 1.2 | 0.7 | 1.3 | 1.1 | 29.7 |

Note: *[1]Refer to Comparative Example A 1.

In Table 2, the determination of the physical property was carried out as shown after Table 1.

EXAMPLE D 5

In the same method as in Example C 5, each of the resin compositions D-A to D-D was coated on the same optical glass fibers, thereby preparing the coated optical glass fibers. No transmission loss of the coated optical glass fibers was observed until −60° C.

(EFFECT OF THE PRESENT INVENTION)

The resin compositions and the coating agents according to the present invention have the advantage of high curing rate, and cured films of the compositions and agents are soft and have low glass transition temperature. Further, the cured films have the advantage of low water absorption and the change of physical property of the cured film is very small over the wide temperature range. Therefore, the resin composition of the present invention is suitable for coating the optical glass fibers for light transmission.

In the case where ε-caprolactone is added to the carbonate diol in the di-(meth)acrylic acid ester, the di-(meth)acrylic acid ester does not become was state easily and the viscosity of it becomes lower whereby the handling becomes easier and the glass transition temperature of the cured composition or agent becomes lower.

What is claimed is:

1. A di-(meth)acrylic acid ester represented by the formula:

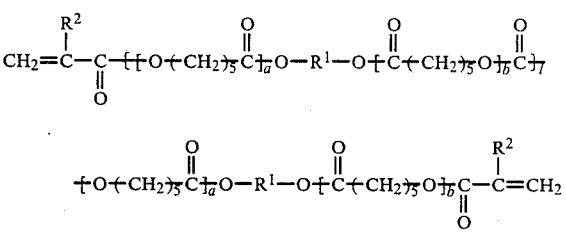

wherein $R^1$ represents an alkylene group having 4 to 10 carbon atoms; $R^2$ represents a hydrogen atom or a methyl group, the mean values of a and b are respectively 0 to 5; the sum value of a plus b is 0.5 to 5 and the mean value of l is 1 to 10.

2. A di-(meth)acrylic acid ester according to claim 1, wherein $R^1$ represents an alkylene group having 5 to 8 carbon atoms; $R^2$ represents a hydrogen atom; the sum value of a plus b is 0.5 to 3 and the mean value of l is 3 to 8.

3. A di-(meth)acrylic acid ester according to claim 1 or 2 wherein $R^1$ represents an alkylene group having 6 carbon atoms.

* * * * *